United States Patent [19]

Khanna et al.

[11] Patent Number: 5,344,825
[45] Date of Patent: Sep. 6, 1994

[54] METHANEDIPHOSPHONIC ACID FORMULATIONS WITH ION EXCHANGERS

[75] Inventors: Satish C. Khanna, Bottmingen; Jonathan Green, Arlesheim, both of Switzerland

[73] Assignee: Ciba-Geigy Corp., Ardsley, N.Y.

[21] Appl. No.: 48,395

[22] Filed: Apr. 14, 1993

[30] Foreign Application Priority Data

Apr. 15, 1992 [CH] Switzerland ............... 1247/92-5

[51] Int. Cl.$^5$ ............ A61K 31/66; A61K 9/50; A61K 9/16
[52] U.S. Cl. ................... 514/108; 514/103; 514/964; 424/419; 424/462; 424/465; 424/468; 424/490; 424/502
[58] Field of Search ............ 424/DIG. 6, 502, 452, 424/455, 462, 465, 483, 484; 514/102, 108, 107, 119, 103

[56] References Cited

U.S. PATENT DOCUMENTS

| | | | |
|---|---|---|---|
| 4,442,231 | 4/1984 | Kataoka et al. | 521/32 |
| 4,621,077 | 11/1986 | Rosini et al. | 514/108 |
| 4,996,047 | 2/1991 | Kelleher et al. | 424/79 |
| 5,002,937 | 3/1991 | Bosies et al. | 514/108 |
| 5,057,505 | 10/1991 | Widler et al. | 514/80 |
| 5,096,717 | 3/1992 | Wirth et al. | 424/490 |
| 5,133,972 | 7/1992 | Ferrini et al. | 424/449 |

OTHER PUBLICATIONS

Reitsma et al "Apposition and Resorption of Bone During Oral Treatment with (3-Amino-1-Hydroxypropylidene)-1, 1-Bisphosphonate (A, Calcif Tissue Int. (1983) 35:357-361.".

H I J Harinck. et al "Paget's Disease of Bone: Early and Late Responses to Three Different Modes of Treatment With Aminohydroxypropylide Bishosphonate (APD)". British Medical Journal vol. 2 Nov. 21, 1987: 1301-1305.

*Primary Examiner*—Marianne M. Cintins
*Assistant Examiner*—T. J. Criares
*Attorney, Agent, or Firm*—Irving M. Fishman; Karen G. Kaiser

[57] ABSTRACT

The invention relates to a novel advantageous oral dosage form for methanediphosphonates, especially the active ingredient disodium pamidronate. A preferred dosage form comprises:

a) disodium-3-amino-1-hydroxypropane-1,1-diphosphonate (disodium pamidronate),
b) a cationic macroporous ion exchange resin based on a styrene/divinylbenzene copolymer having an exchangeable aminophosphonate group and, where appropriate,
c) further pharmaceutically acceptable excipients.

The ingredients can be processed to form tablets, dragées, capsules etc.

13 Claims, No Drawings

METHANEDIPHOSPHONIC ACID FORMULATIONS WITH ION EXCHANGERS

The invention relates to an especially advantageous oral dosage form for methanediphosphonic acid derivatives, to processes for the preparation of that dosage form, and to the use of that dosage form in a therapeutic method for the alleviation of disorders of calcium metabolism.

Numerous methanediphosphonic acid derivatives of different structure are known. For example 3-amino-1-hydroxypropane-1,1-diphosphonic acid and its salts, processes for the preparation of that acid, and its commercial use as a calcium complex-forming component of a detergent composition have been described in German Published Patent Specification No. 2 130 794. The suitability of the said acid and its salts as a pharmaceutical active ingredient is described in German Published Patent Application No. 2 405 254. The disodium salt—referred to hereinafter as disodium pamidronate (generic name)—has already undergone clinical investigation as an antihypercalcaemic drug. Numerous publications demonstrate the pronounced activity of methanediphosphonic acid derivatives against especially serious conditions such as osteoporosis, osteolysis as a sequel to metastasis in bony substance, and Paget's disease.

An antihypercalcaemically active compound should in addition be suitable for long-term therapy which may last up to several months or years. For such long periods of administration it is necessary to provide suitable dosage forms that can be administered by the patient without assistance, outside the clinical area. Peroral dosage forms, such as tablets, dragées or capsules, can meet those requirements.

From in-vivo findings using rats, the active ingredient disodium pamidronate is known to have a low absorption capacity after oral administration of approximately 0.2%, see P. H. Reitsma et al. in Calcified Tissue Int. (1983) 35: 357–361. A high dose of that active ingredient would therefore be necessary in oral dosage forms, but that has disadvantages since in the British Medical J., Volume 295, 1301–1305 (1987), see page 1304, "epigastric complaints" are mentioned in clinical tests carried out on patients after the administration of capsules or tablets comprising disodium pamidronate. Similar problems are known with other methanediphosphonic acid derivatives. There is therefore a great need for low-dose oral dosage forms with improved gastric tolerance of the active ingredient.

There are described in published European Patent Application No. 421 921 double-coated granules, especially pellets comprising the active ingredient disodium pamidronate that are coated with a hydrophilic elastic inner coating and an enteric outer coating that is soluble in intestinal juice. Those granules or pellets which, introduced into capsules, can be administered orally, are indeed distinguished by improved gastric tolerance. Release is delayed and occurs in the duodenum, after passage through the stomach, as a result of the enteric outer coating being slowly dissolved by the action of intestinal juice, so that absorption of the active ingredient does not occur until that region of the gastrointestinal tract is reached.

In view of the controlled-release effect of that dosage form, however, the active ingredient still has to be administered in high doses (higher than approximately 150 mg of active ingredient per unit dose form) in spite of the risk of damage to the mucosa of the duodenum. Based on the total length of time taken to pass through the gastrointestinal tract, the controlled-release effect has the result of reducing the time available for the absorption process. That reduction in time is compensated by an increase in dose in order to achieve a therapeutically effective reduction in the level of calcium in the plasma in the remaining time available for the absorption process.

The aim of the present invention is the preparation of a low-dose dosage form with preferably less than 150 mg, especially less than 100 mg, of active ingredient per unit dose form. With such a reduced dose, there is a reduced risk of damage to the mucosa over the entire gastrointestinal tract and of the occurrence of other complaints, such as nausea.

That aim is achieved by the present invention, which relates to a pharmaceutical composition comprising a) a methanediphosphonic acid derivative of formula:

wherein one of $R_1$ and $R_2$ is hydrogen or hydroxy and the other is amino-$C_{1-4}$alkyl, $C_{2-6}$alkyleneamino-$C_{1-4}$alkyl, N-mono- or N,N-di-$C_{1-8}$alkylamino-$C_{2-4}$alkyl, $C_{5-7}$cycloalkylamino, heteroaryl-$C_{1-4}$alkyl or N-$C_{1-4}$alkyl-N-phenylthio-$C_{1-4}$alkylamino-$C_{1-4}$alkyl, or a salt thereof, b) a cationic macroporous ion exchange resin based on a styrene/divinylbenzene copolymer having an exchangeable aminophosphonate group and, where appropriate, c) further pharmaceutically acceptable excipients.

In an especially preferred embodiment, the pharmaceutical composition comprises disodium pamidronate in a dose per unit dose form of 50–100 mg, especially 50–80 mg, in admixture with the cationic ion exchange resin Duolite ® (Trade Mark of Rohm & Haas) C 467.

The pharmaceutical composition is preferably administrable in the form of tablets, dragées or capsules and is distinguished by an especially marked reduction in the level of calcium in the plasma. In-vivo findings using rats have shown that, with the new dosage form, the capacity for absorption of the active ingredient when methanediphosphonic acid derivatives are administered orally in an oily or aqueous suspension in admixture with an excess of ion exchange resin based on the active ingredient in a ratio by weight of 1:10 is more than six times greater compared with an orally administered aqueous suspension of the active ingredient. The effective dose ascertained from in-vivo findings is approximately 8 mg/kg (p.o.).

The terms and definitions used hereinbefore and hereinafter preferably have the following meanings within the scope of the description of the invention:

The term "pharmaceutical composition" defines mixtures of methanediphosphonic acid derivatives (I) with resin particles of the cationic ion exchanger defined hereinbefore and, where appropriate, customary pharmaceutical excipients, that can be processed into oral dosage forms, such as tablets, capsules or dragées.

The present invention also relates to a process for the preparation of the pharmaceutical composition, which comprises mixing together a) at least one methanediphosphonic acid derivative (I) and
b) resin particles of a cationic macroporous ion exchanger based on a styrene/divinylbenzene copolymer having an exchangeable aminophosphonate group and, where appropriate,
c) further pharmaceutically acceptable excipients, and further processing the mixture to produce an oral dosage form.

In a compound (I), amino-$C_{1-4}$alkyl is preferably 2-amino-1-ethyl or 3-amino-1-propyl.

$C_{2-6}$Alkyleneamino-$C_{1-4}$alkyl is preferably 2-($\alpha\omega$-$C_{2-4}$alkyleneamino)-1-ethyl, e.g. 2-(1,4-butyleneamino)-1-ethyl.

N-Mono- or N,N-di-$C_{1-8}$alkylamino-$C_{2-4}$alkyl is preferably 2-(N-$C_{1-4}$alkyl-N-$C_{4-8}$alkyl-amino)-1-ethyl, e.g. 2-(N-methyl-N-n-pentylamino)-1-ethyl.

$C_{5-7}$Cycloalkylamino is preferably cycloheptyl- or cyclohexyl-amino.

Heteroaryl-$C_{1-4}$alkyl is preferably azaaryl-$C_{1-4}$alkyl having five or six ring members, e.g. 2-, 3- or 4-pyridylmethyl.

N-$C_{1-4}$Alkyl-N-phenylthio-$C_{1-4}$alkylamino-$C_{1-4}$alkyl is e.g. 2-[N-methyl-N-(2-phenyl-thio-1-ethyl)-amino]-1-ethyl.

Salts of methanediphosphonic acid derivatives are especially pharmaceutically acceptable salts formed with amines, but are especially alkali metal salts, e.g. sodium or potassium salts.

The following compounds are especially preferred:
3-Amino-1-hydroxypropane-1,1-diphosphonic acid, 4-amino-1-hydroxy-n-butane-1,1-diphosphonic acid, 3-(1,4-butyleneamino)-1-hydroxypropane-1,1-diphosphonic acid, 1-hydroxy-3-(N-methyl-N-n-pentylamino)-propane-1,1-diphosphonic acid, 1-cyclohexyl-aminomethane-1,1-diphosphonic acid, 1-hydroxy-2-(3-pyridyl)-ethane-1,1-diphosphonic acid, 1-hydroxy-3-[N-methyl-N-(2-phenylthio-1-ethyl)-amino]-propane-1,1-diphosphonic acid and salts of those compounds.

The especially preferred component a) disodium 3-amino-1-hydroxypropane-1,1-diphosphonate (disodium pamidronate) in the pharmaceutical composition is preferably in the form of the crystalline hydrate, preferably the pentahydrate, the preparation and characteristic data of which are described in published European Patent Application 177 443.

An advantageous oral dose has about 20–150 mg, especially about 50–100 mg, more especially about 50–80 mg of active ingredient per unit dose form.

Component b) consists of resin particles of a cationic, microporous or, preferably, macroporous ion exchanger based on a styrene/divinylbenzene copolymer having an exchangeable aminophosphonate group. The matrix consists of polymerised styrene swellable in the aqueous phase with divinylbenzene as crosslinking agent and functional aminophosphonate groups that are charged with exchangeable cations, especially sodium ions. In the commercial product Duolite ® C 467, the aminophosphonate group consists of the phosphonic acid methylaminomethyl group ($-CH_2-NH-CH_2-PO_3H_2$) in the form of the cation-exchangeable mono- or di-sodium salt ($-CH_2-NH-CH_2-PO_3HNa$ or $-CH_2-NH-CH_2-PO_3Na_2$). The characteristic data of the commercial product Duolite ® C 467 are as follows:

| | |
|---|---|
| external appearance | beige-coloured beads |
| ionic form | $Na^+$ |
| exchange capacity | 1 equivalent per liter ($Na^+$ form) |
| | 1.4 equivalents per liter ($H^+$ form) |
| specific weight | 1.12 ($Na^+$ form) |
| suspension | 740 g/l |
| particle size | 0.3–1 mm |
| swelling capacity | 35% ($H^+$ form $\rightarrow Na^+$ form) |

The characteristic data were taken from Product Data Sheet DTS 0092 A (published in June 1991) of Rohm & Haas.

The average particle size of the resin particles is about 1–200 μm, especially 10–100 μm. The crosslinking is about 2–8%, preferably 2–4%.

In a special embodiment, the mixing ratio of methanediphosphonic acid derivative (I) to resin particles of the ion exchanger is about 1:1 to 1:100, preferably about 1:1 to 1:20, especially 1:1 to 1:10.

Component c) consists of pharmaceutically acceptable excipients that can be used for the preparation of oral dosage forms, e.g. solid unit dose forms, such as tablets, dragées, capsules or sachets, but also of liquid dosage forms, such as syrups, drops, suspensions, emulsions etc.

Tablets are obtained by the direct compression of components a) and b) with customary excipients, such as lactose, mannitol, microcrystalline cellulose or talc, or preferably by the compression of granules.

Granules are also solid medicament preparations that comprise the methanediphosphonic acid derivative (I) and the ion exchange resin defined hereinbefore and such excipients as are customary in the pharmaceutical technology of tabletting processes. The granules according to the present invention can also themselves be used as oral dosage forms when introduced, for example, into capsules or sachets, but they are preferably further processed to form tablets.

Suitable excipients for the preparation of granules are, e.g., pulverulent fillers with flow-regulating properties, e.g. talc, silicon dioxide, e.g. synthetic amorphous dehydrated silicic acid of the type Syloid ® (Grace), e.g. SYLOID 244 FP, microcrystalline cellulose, e.g. of the type Avicel ® (FMC Corp.), e.g. the types AVICEL PH 101, 102, 105, RC 581 or RC 591, Emcocel ® (Mendell Corp.) or Elcema ® (Degussa), carbohydrates such as sugars, sugar alcohols, starch or starch derivatives, e.g. lactose, dextrose, saccharose, glucose, sorbitol, mannitol, xylitol, potato starch, corn starch, rice starch or wheat starch or amylopectin, tricalcium phosphate, calcium hydrogen phosphate or magnesium trisilicate, binders such as gelatin, tragacanth, agar, alginic acid, cellulose ethers, e.g. methylcellulose, carboxymethylcellulose or hydroxypropylmethylcellulose, polyethylene glycols or ethylene oxide homopolymers, especially having a degree of polymerisation of about $2.0 \times 10^3$–$1.0 \times 10^5$ and an approximate molecular weight of about $1.0 \times 10^5$–$5.0 \times 10^6$, e.g. excipients known by the name of Polyox ® (Union Carbide), polyvinylpyrrolidone or povidones, especially having a mean molecular weight of about 10 000–360 000, polyvinyl alcohol having a degree of hydrolysis of about 95–99% and a degree of polymerisation of about 500–2500, and agar or gelatin, surface-active substances, e.g. anionic surfactants of the alkyl sulfate type, e.g. sodium, potassium or magnesium n-dodecyl sulfate, n-tetradecyl sulfate, n-hexadecyl sulfate or n-octadecyl sulfate, of the alkyl ether sulfate type, e.g. sodium, potassium or magnesium n-dodecyloxyethyl sulfate, n-tetradecyloxyethyl sulfate, n-hexadecyloxyethyl sulfate or n-octadecyloxyethyl sulfate, or of the alkanesulfonate type, e.g. sodium, potassium or magnesium n-dodecanesulfonate, n-tetradecane-sulfonate, n-hexadecanesulfonate or n-octadecanesulfonate, non-ionic surfactants of the fatty acid polyhydroxyalcohol ester type, such as sorbitan mono-laurate, -oleate, -stearate or -palmitate, sorbitan tristearate or trioleate, polyoxyethylene adducts of fatty acid polyhydroxyalcohol esters, such as polyoxyethylene sorbitan mono-laurate, -oleate, -stearate -palmitate, tristearate or trioleate, polyethylene glycol fatty acid esters, such as polyoxyethyl stearate, polyethylene glycol 400 stearate, polyethylene glycol 2000 stearate, especially ethylene oxide/propylene oxide block polymers of the type Pluronics ® (BWC) or Synperonic ® (ICI).

In a special embodiment tablets may also comprise excipients that are customary for the preparation of effervescent tablets, that is to say, in each case at least one excipient capable of releasing $CO_2$ and at least one excipient capable of inducing the release of $CO_2$.

An excipient capable of releasing $CO_2$ is, e.g., a pharmaceutically acceptable mono- or di-basic salt of carbonic acid, e.g. sodium or potassium carbonate, especially sodium hydrogen carbonate.

An excipient that induces the release of $CO_2$ is, e.g., a pharmaceutically acceptable acid that is in solid form and can be formulated into tablets with the active ingredient, the ion exchange resin and other excipients without the evolution of gas. A suitable acid is, e.g., tartaric acid, malic acid, fumaric acid, adipic acid, succinic acid, ascorbic acid or maleic acid. Citric acid is preferred.

The preparation of granules with the ion exchange resin defined hereinbefore is carried out in a manner known per se especially by wet granulation methods.

Such processes proceed continuously, e.g. by means of simultaneous spraying with granulating solution of the mass to be granulated and drying, e.g. in a drum granulator, in granulating vessels, on dish granulators, in a fluid bed, by spray-drying or spray-solidifying, or proceed discontinuously, as, for example, in a fluidised bed, a batch mixer or a spray-drying drum.

Processes that can be carried out discontinuously are preferred, the mass to be granulated first of all forming a moist aggregate with the granulating solution fed in and the aggregate then being comminuted to form granules of the desired particle size using known extrusion and spheronisation processes. Suitable extruders and spheronisers are, e.g. apparatus produced by Wyss & Probst, Werner & Pfleiderer, HKD, Loser, Fuji, Nica, Caleva inter alia.

The mass to be granulated consists of comminuted, preferably ground, ion exchanger defined hereinbefore, preferably having a mean particle size of less than 400 $\mu m$ (more than 90%), and the excipients mentioned hereinbefore, e.g. pulverulent fillers, such as microcrystalline cellulose of the AVICEL type. AVICEL P-H 102 is especially suitable. Depending on the process employed, the mass to be granulated can be premixed or can be obtained by admixing APD-$Na_2$ with the ion exchange resin and with one or more excipients, or by admixing the excipients with the active ingredient.

The compression of the granules to form tablet cores can be carried out in conventional tabletting machines, preferably eccentric presses and rotary presses, especially EKO-Korsch eccentric tabletting machines, at an operating pressure of about 10 kN or more. Dragées are produced e.g. by coating tablet cores with a film or coating layer of the particular thickness required using the known fluidised bed process, in confectioning vessels or according to coacervation processes.

The coating agent is, for example, dissolved or suspended in water in the desired proportion. Where appropriate, excipients such as polyethylene glycol are added. The solution or dispersion is sprayed onto the dragée or tablet cores with other excipients, e.g. talc or silicon dioxide, e.g. SYLOID 244 FP, e.g. using known processes, such as fluidised bed spray-coating, e.g. in systems produced by Aeromatic, Glatt, Wurster or Hüttlin (ball coaters) or in a vessel according to the processes known by the names Accela Cota.

Capsules are preferably dry-filled capsules made of gelatin, especially hard gelatin, which are prepared where appropriate with the addition of glycerol or sorbitol, are dissolved without time delay by the action of gastric juice and release components a) and b). Capsules may comprise components a) and b) in the form of a mixture or in the form of granules. Other excipients and fillers, such as lactose, starch, and glidants such as starch or magnesium stearate, may be admixed. Soft capsules may, in addition, contain liquids, such as lecithin, fats, oils, paraffin oil or liquid polyethylene glycol. Dry-filled capsules size 0–4, preferably 0–2, are suitable, depending on the dose. Commercial products produced by Eli Lilly, Elanco, Capsugel or Scherer are suitable.

In a specific embodiment, the capsules may contain pellets, which are obtainable in accordance with the granulating processes described hereinbefore by subjecting the still moist mass to be granulated to extrusion or spheronisation processes to obtain regularly shaped, preferably spheroidal, granules in the form of pellets. A mean particle size of about 0.5 to 1.25 mm is preferred.

Sachets are receptacles, for example bags made of polyethylene, lined paper or aluminium, that contain the components a) and b), e.g. lecithin. The mixture can be removed directly after opening the sachet and administered orally, e.g. mixed with water. Components a) and b) can also be contained in the form of granules or pellets in the said capsules and sachets.

The solid dosage forms described hereinbefore can be of different shapes, e.g. of a round, oval, oblong or cylindrical shape, and of different sizes depending on the amount of active ingredient they contain. They may furthermore be transparent, colourless or coloured and, if desired, inscribed to give the products an individual appearance and allow immediate recognition. The use of dyestuffs can serve both to enhance the appearance and to characterise the preparation.

Liquid dosage forms are e.g. syrups, which are prepared by conventional mixing process such as those described in Hagers Handbuch der Pharmazeutischen Praxis, Springer Verlag, volume VII, part A, pages 640–644, or in Remington's Phamaceutical Sciences, Mack 1985, pages 1500–1503. An aqueous suspension of the ion exchange resin with the ground active ingredient is first of all produced, and excipients, such as the mentioned wetting agents, viscosity-increasing substances (thickeners), preservatives, antioxidants, dyestuffs, flavour enhancers (flavourings), sugars and sweeteners are added to that suspension. Particles of ion exchange resins of a suitable size, e.g. larger than 1 $\mu m$ and smaller than 100 $\mu m$, can, if desired, be produced by grinding.

Conventional methods indicated in standard works such as Hagers Handbuch der Pharmazeutischen Praxis or Remington's Pharmaceutical Sciences can be used to produce oral liquid dosage forms, such as drops, suspensions, emulsions etc.

The pharmaceutical compositions according to the present invention are, on account of the advantageously low dose, distinguished by especially good gastrointestinal tolerance, especially of the active ingredient disodium pamidronate. The dosage forms mentioned hereinbefore are suitable for the treatment of diseases that may be associated with disorders of calcium metabolism, for example inflammatory processes in joints, degenerative processes in articular cartilages, osteoporosis, periodontitis, hyperparathyroidism, and for the treatment of calcium deposits in blood vessels or on prosthetic implants. Also favourably influenced are diseases in which an anomalous deposit of sparingly soluble calcium salts is to be observed, such as those of the arthritis type, e.g. Bechterew's disease, neuritis, bursitis, periodontitis and tendinitis; fibrodysplasia, osteoarthrosis or arteriosclerosis, as well as diseases in which an anomalous dissolution of hard body tissue is prominent, such as hereditary hypophosphatasia, degenerative processes in articular cartilages, osteoporosis of various kinds, Paget's disease and osteodystrophia fibrosa, as well as osteolytic processes induced by tumours and also hypercalcaemia.

The present invention therefore also relates to the use of pharmaceutical solid dosage forms in a therapeutic or prophylactic method for the human or animal body.

The following Examples illustrate the invention. Disodium pamidronate is abbreviated to APD-Na$_2$.

EXAMPLE 1

Formulation for film-coated dragées. The amounts quoted are per unit dose form.

| Film-coated dragée core | |
| --- | --- |
| APD-Na$_2$ (active ingredient) | 75.0 mg |
| DUOLITE C 467 cationic ion exchange resin | 425.0 mg |
| microcrystalline cellulose AVICEL PH 102 | 75.0 mg |
| cottonseed oil hydr. CUTINA | 15.0 mg |
| | 590.0 mg |

| Protective film-coating | |
| --- | --- |
| METHOCEL cellulose HPMC 603 | 10.0 mg |
| talc | 9.5 mg |
| CREMOPHOR PH 40 | 0.5 mg |
| Film-coated dragée having protective film-coating | 610.0 mg |

Preparation: The cationic ion exchange resin is ground to an average particle size of 10 μm in an air-jet mill. 425 g of ion exchange resin are mixed with 75 g of active ingredient and 75 g of microcrystalline cellulose for ten minutes in a planet mixer (Knedwood), 15 g of cottonseed oil are added, and the batch is comminuted through a 0.5 mm sieve and mixed again for 5 minutes. The mixture is compressed in an eccentric press EKO (punch size 11.5 mm). The cores are coated in a fluidised bed (Strea 1) with the protective film-coating of the composition indicated.

EXAMPLE 2

Formulation for capsule filling (liquid). The amounts quoted are per unit dose form.

| APD-Na$_2$ (active ingredient) | 75.0 mg |
| --- | --- |
| DUOLITE C 467 cationic ion exchange resin | 275.0 mg |
| groundnut oil | 120.0 mg |
| beeswax | 30.0 mg |
| capsule filling mass | 500.0 mg |
| Hard gelatin capsule size 0 | |

Preparation: 275 g of cationic ion exchange resin are ground as indicated in Example 1 and mixed with 75 g of active ingredient and 120 g of groundnut oil. This mixture is introduced in a liquid-filling station (Höflinger & Karg) into size 0 hard gelatin capsules.

EXAMPLE 3

Formulation for pellets. The amounts quoted are per unit dose form.

| Pellet cores | |
| --- | --- |
| APD-Na$_2$ (active ingredient) | 75.0 mg |
| DUOLITE C 467 cationic ion exchange resin | 275.0 mg |
| microcrystalline cellulose AVICEL PH 102 | 48.0 mg |
| | 398.0 mg |
| Protective film-coating | |
| cellulose ether METHOCEL HPM 603 | 5.0 mg |
| talc | 4.75 mg |
| CREMOPHOR PH 40 | 0.25 mg |
| Basic pellet having protective film-coating | 408.0 mg |

Preparation: 275 g of cationic ion exchange resin are ground as indicated in Example 1 and mixed with 75 g of active ingredient and 48 g of microcrystalline cellulose. The mixture is moistened with demineralised water, extruded and pelleted. The pellets are coated in a fluidised bed (Strea 1) with the protective film-coating of the composition indicated.

EXAMPLE 4

Formulation for film-coated dragées. The amounts are given per unit dose form.

| 1-Hydroxy-3-(N-methyl-N-n-pentylamino)-propane-1,1-diphosphonic acid | 20,0 mg |
| --- | --- |
| DUOLITE C 467 cation.ion exchange resin | 200,0 mg |
| SOFTISAN | 50,0 mg |
| MIGLYOL | 200,0 mg |
| capsule filling mass | 470,0 mg |
| Hard gelatin capsule size 0 | |

20,0 mg active ingredient and 200 g DUOLITE are ground in an air suspension mill and mixed with the given additives. The paste is filled into size 0 hard gelatine capsules.M

EXAMPLE 5

Formulation for film-coated dragées. The amounts are given per unit dose form.

| 1-Hydroxy-2-(3-pyridyl)-ethane-1,1-diphosphonic acid | 20,0 mg |
| --- | --- |
| DUOLITE C 467 cation. ion exchange resin | 150,0 mg |
| soy bean lecithin | 10,0 mg |
| sesame oil | 250,0 mg |
| capsule filling mass | 430,0 mg |
| Hard gelatin capsule size 0 | |

10 g soy bean lecithin are dissolved in 250 g sesame oil. 150 g DUOLITE are dispersed therein and wet ground in a sand mill. The calculated amount of active ingredient is added and the mixture is introduced into a liquid-filling station (Höflinger & Karg) into size 0 hard gelatine capsules.

What is claimed is:

1. A pharmaceutical composition for the oral administration of methanediphosphonic acid derivatives, comprising a) a methanediphosphonic acid derivative of formula:

$$R_1-\underset{\underset{PO_3H_2}{|}}{\overset{\overset{PO_3H_2}{|}}{C}}-R_2, \qquad (I)$$

wherein one of $R_1$ and $R_2$ is hydrogen or hydroxy and the other is amino-$C_{1-4}$alkyl, $C_{2-6}$alkyleneamino-$C_{1-4}$alkyl, N-mono- or N,N-di-$C_{1-8}$alkylamino-$C_{2-4}$alkyl, $C_{5-7}$cycloalkylamino, heteroaryl-$C_{1-4}$alkyl or N-$C_{1-4}$alkyl-N-phenylthio-$C_{1-4}$alkylamino-$C_{1-4}$alkyl, or a pharmaceutically acceptable salt thereof, b) a cationic macroporous ion exchange resin based on a styrene/divinylbenzene copolymer having an exchangeable phosphonic acid methylaminomethyl group in the form of the cation-exchangeable mono- or di-sodium salt in an amount which enhances the abosorption of a), and, c) pharmaceutically acceptable excipients.

2. A pharmaceutical composition according to claim 1, comprising wherein, in component a) one of $R_1$ and $R_2$ is hydrogen or hydroxy and the other is 2-amino-1-ethyl, 3-amino-1-propyl, 2-(1,4-butyleneamino)-1-ethyl, 2-(N-methyl-N-n-pentylamino)-1-ethyl, cycloheptyl- or cyclohexylamino, 2-, 3- or 4-pyridylmethyl or [N-methyl-N-(2-phenylthio-1-ethyl)-amino]-1-ethyl.

3. A pharmaceutical composition according to claim 1, wherein a) is 3-amino-1-hydroxypropane-1-diphosphonic acid, 4-amino-1-hydroxy-n-butane-1,1-diphosphonic acid, 3-(1,4-butyleneamino)-1-hydroxypropane-1,1-diphosphonic acid, 1-hydroxy-3-(N-methyl-(N-n-pentylamino)-propane-1,1-diphosphonic acid, 1-cyclohexylaminomethane-1,1-diphosphonic acid, 1-hydroxy-2-(3-pyridyl)-ethane-1,1-diphosphonic acid, 1-hydroxy-3[N-methyl-N-(2-phenylthio-1-ethyl)-amino]-propane-1,1-diphosphonic acid or a salt of such a compound.

4. A pharmaceutical composition according to claim 1, wherein a) is the crystalline pentahydrate of disodium pamidronate.

5. A pharmaceutical composition according to claim 4, wherein a) the crystalline pentahydrate of disodium pamidronate is in a dose of 50–100 mg per unit dose form.

6. A pharmaceutical composition according to claim 5, wherein a) the crystalline pentahydrate of disodium pamidronate is in a dose of 50–80 mg per unit dose form.

7. A pharmaceutical composition according to claim 1, wherein the mixing ratio of compound (I) to the resin particles of the ion exchanger is from 1:1 to 1:100.

8. A pharmaceutical composition according to claim 7, wherein the mixing ratio of compound (I) to the resin particles of the ion exchanger is from 1:1 to 1:20.

9. A pharmaceutical composition according to claim 8, wherein the mixing ratio of compound (I) to the resin particles of the ion exchanger is from 1:1 to 1:10.

10. A pharmaceutical composition according to claim 1 in the form of tablets, capsules, dragées or pellets.

11. A process for the preparation of a pharmaceutical composition for the oral administration of a methanediphosphonic acid derivative, which comprises mixing together a) a compound of formula I, $$R_1-\underset{\underset{PO_3H_2}{|}}{\overset{\overset{PO_3H_2}{|}}{C}}-R_2 \qquad (I)$$

b) resin particles of a cationic ion exchanger based on a styrene/divinylbenzene copolymer having an exchangeable phosphonic acid methylaminomethyl group in the form of the cation-exchangeable mono- or di-sodium salt in an amount which enhances the absorption of a), and c) pharmaceutically acceptable excipients, and processing the mixture to produce an oral dosage form.

12. A process according to claim 11, wherein the crystalline pentahydrate of disodium pamidronate a), mixed with the resin particles b), and the excipients c) is processed to form tablets, capsules, dragées or pellets.

13. A method for treating a disease selected from those associated with disorders of calcium, phosphate or both calcium and phosphate metabolism comprising administering to an animal in need of such treatment a pharmaceutical composition according to claim 1.

* * * * *

UNITED STATES PATENT AND TRADEMARK OFFICE
CERTIFICATE OF CORRECTION

PATENT NO. : 5,344,825
DATED : September 6, 1994
INVENTOR(S) : Khanna et al

It is certified that error appears in the above-indentified patent and that said Letters Patent is hereby corrected as shown below:

In column 9, line 32, after "claim 1," delete "comprising"

In column 9, lines 40-41, delete "3-amino-1-hydroxy-propane-1-diphosphonic acid" and insert --3-amino-1-hydroxy-propane-1,1-diphosphonic acid-- in lieu thereof Signed and Sealed this Twenty-ninth Day of November, 1994

Attest:

BRUCE LEHMAN

Attesting Officer          Commissioner of Patents and Trademarks